(12) United States Patent
Lorenzo et al.

(10) Patent No.: US 11,039,944 B2
(45) Date of Patent: Jun. 22, 2021

(54) BRAIDED STENT SYSTEM WITH ONE OR MORE EXPANSION RINGS

(71) Applicant: DePuy Synthes Products, Inc., Raynham, MA (US)

(72) Inventors: Juan Lorenzo, Raynham, MA (US); Peter Forsythe, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 184 days.

(21) Appl. No.: 16/234,226

(22) Filed: Dec. 27, 2018

(65) Prior Publication Data
US 2020/0206003 A1    Jul. 2, 2020

(51) Int. Cl.
*A61F 2/90* (2013.01)
*A61B 17/12* (2006.01)

(52) U.S. Cl.
CPC ............ *A61F 2/90* (2013.01); *A61B 17/1214* (2013.01); *A61B 17/12118* (2013.01); *A61B 17/12031* (2013.01)

(58) Field of Classification Search
CPC ......... A61F 2002/823–2002/828; A61F 2/852; A61F 2/86–2/90; A61F 2220/0025; A61F 2220/0075; A61F 2250/001; A61F 2250/0018; A61F 2250/0036; A61F 2250/0063; A61B 17/12118; A61B 17/1214
See application file for complete search history.

(56) References Cited

U.S. PATENT DOCUMENTS

| | | |
|---|---|---|
| 4,332,278 A | 4/1982 | Lalikos |
| 4,610,688 A | 9/1986 | Silvestrini |
| 4,754,685 A | 7/1988 | Kite |
| 5,064,435 A | 11/1991 | Porter |
| 5,275,622 A | 1/1994 | Lazarus et al. |
| 5,282,824 A | 2/1994 | Gianturco |
| 5,330,500 A | 7/1994 | Song |
| 5,382,259 A | 1/1995 | Phelps et al. |

(Continued)

FOREIGN PATENT DOCUMENTS

| | | |
|---|---|---|
| EP | 2 777 642 A1 | 9/2014 |
| EP | 2777649 A1 | 9/2014 |

(Continued)

OTHER PUBLICATIONS

Extended European Search Report issued in corresponding European Patent Application No. 19 21 9438 dated Apr. 7, 2020.

(Continued)

*Primary Examiner* — Paul B Prebilic
(74) *Attorney, Agent, or Firm* — Troutman Pepper Hamilton Sanders LLP

(57) ABSTRACT

An endovascular self-expanding stent system that can include a braid with a proximal end, a distal end, and a lumen formed therebetween. The braid can be formed from one or more wires woven to comprise interstices. A first expansion ring can be connected to the proximal end of the braid. A second expansion ring can be connected to the distal end of the braid. Each expansion ring can include a frame that imparts an outwardly expanding radial force to the braid. The frame can include a plurality of elongate members interconnected by one or more intersections.

7 Claims, 10 Drawing Sheets

(56) References Cited

U.S. PATENT DOCUMENTS

| | | |
|---|---|---|
| 5,387,235 A | 2/1995 | Chuter |
| 5,423,849 A | 6/1995 | Engelson |
| 5,476,508 A | 12/1995 | Amstrup |
| 5,522,881 A | 6/1996 | Lentz |
| 5,549,662 A | 8/1996 | Fordenbacher |
| 5,556,413 A | 9/1996 | Lam |
| 5,601,593 A | 2/1997 | Freitag |
| 5,609,627 A | 3/1997 | Goicoechea |
| 5,645,558 A | 7/1997 | Horton |
| 5,662,622 A | 9/1997 | Gore |
| 5,702,418 A | 12/1997 | Ravenscroft |
| 5,725,549 A | 3/1998 | Lam |
| 5,728,131 A | 3/1998 | Frantzen |
| 5,755,772 A | 5/1998 | Evans et al. |
| 5,769,887 A | 6/1998 | Brown |
| 5,776,161 A | 7/1998 | Globerman |
| 5,817,126 A | 10/1998 | Imran |
| 5,849,037 A | 12/1998 | Frid |
| 5,851,217 A | 12/1998 | Wolff |
| 5,899,935 A | 5/1999 | Ding |
| 5,916,235 A | 6/1999 | Guglielmi |
| 5,916,264 A | 6/1999 | Von Oepen |
| 5,961,546 A * | 10/1999 | Robinson .................. A61F 2/07 623/1.14 |
| 6,010,529 A | 1/2000 | Herweck |
| 6,015,432 A | 1/2000 | Rakos et al. |
| 6,033,436 A | 3/2000 | Steinke |
| 6,036,725 A | 3/2000 | Avellanet |
| 6,051,020 A | 4/2000 | Goicoechea |
| 6,099,559 A | 8/2000 | Nolting |
| 6,110,198 A | 8/2000 | Fogarty |
| 6,123,722 A | 9/2000 | Fogarty et al. |
| 6,123,723 A | 9/2000 | Konya et al. |
| 6,152,956 A | 11/2000 | Pierce |
| 6,161,399 A | 12/2000 | Jayaraman |
| 6,165,213 A | 12/2000 | Goicoechea |
| 6,168,621 B1 | 1/2001 | Vrba |
| 6,176,875 B1 | 1/2001 | Lenker |
| 6,264,683 B1 | 7/2001 | Stack et al. |
| 6,280,465 B1 | 8/2001 | Cryer |
| 6,319,278 B1 | 11/2001 | Quinn |
| 6,325,823 B1 | 12/2001 | Horzewski |
| 6,348,066 B1 | 2/2002 | Pinchuk et al. |
| 6,409,755 B1 | 6/2002 | Vrba |
| 6,488,702 B1 | 12/2002 | Besselink |
| 6,612,012 B2 | 9/2003 | Mitelberg et al. |
| 6,626,936 B2 | 9/2003 | Stinson |
| 6,635,080 B1 | 10/2003 | Lauterjung et al. |
| 6,673,106 B2 | 1/2004 | Mitelberg |
| 6,699,277 B1 | 3/2004 | Freidberg et al. |
| 6,740,113 B2 | 5/2004 | Vrba |
| 6,673,107 B1 | 6/2004 | Brandt |
| 6,770,089 B1 | 8/2004 | Hong et al. |
| 6,818,013 B2 | 11/2004 | Mitelberg |
| 6,833,003 B2 | 12/2004 | Jones |
| 6,899,914 B2 | 5/2005 | Schmitz |
| 6,911,040 B2 | 6/2005 | Johnson et al. |
| 6,918,928 B2 | 7/2005 | Wolinsky |
| 6,929,659 B2 | 8/2005 | Pinchuk |
| 6,945,994 B2 | 9/2005 | Austin et al. |
| 6,955,685 B2 | 10/2005 | Escamilla |
| 6,960,227 B2 | 11/2005 | Jones |
| 6,960,228 B2 | 11/2005 | Mitelberg et al. |
| 6,970,734 B2 | 11/2005 | Eidenschink |
| 7,001,422 B2 | 2/2006 | Escamilla |
| 7,037,331 B2 | 5/2006 | Mitelberg |
| 7,122,052 B2 | 10/2006 | Greenhaigh |
| 7,201,769 B2 | 4/2007 | Jones et al. |
| 7,208,008 B2 | 4/2007 | Clarke |
| 7,267,685 B2 | 9/2007 | Butaric |
| 7,288,111 B1 | 10/2007 | Holloway et al. |
| 7,291,167 B2 | 11/2007 | DiCaprio |
| 7,309,351 B2 | 12/2007 | Escamilla et al. |
| 7,344,559 B2 | 3/2008 | Gray |
| 7,462,190 B2 | 12/2008 | Lombardi |
| 7,480,973 B2 | 1/2009 | Miller |
| 7,628,806 B2 | 12/2009 | Yampolsky et al. |
| 7,632,302 B2 | 12/2009 | Vreeman et al. |
| 7,641,647 B2 | 1/2010 | Gunderson |
| 7,655,031 B2 | 2/2010 | Tenne et al. |
| 7,655,034 B2 | 2/2010 | Mitchell et al. |
| 7,708,773 B2 | 5/2010 | Pinchuk et al. |
| 7,758,629 B2 | 7/2010 | Holloway et al. |
| 7,761,138 B2 | 7/2010 | Wang |
| 7,806,919 B2 | 10/2010 | Bloom et al. |
| 7,806,923 B2 | 10/2010 | Moloney |
| RE42,244 E | 3/2011 | Boatman |
| 7,913,371 B2 | 3/2011 | Klocke |
| 7,985,213 B2 | 7/2011 | Parker |
| 7,998,187 B2 | 8/2011 | Hartley et al. |
| 8,021,418 B2 | 9/2011 | Gerberding |
| 8,043,353 B2 | 10/2011 | Kaufmann et al. |
| 8,043,357 B2 | 10/2011 | Hartley |
| 8,048,139 B2 | 11/2011 | Frid et al. |
| 8,092,510 B2 | 1/2012 | Metcalf et al. |
| 8,142,456 B2 | 3/2012 | Rosqueta |
| 8,152,833 B2 | 4/2012 | Zaver |
| 8,182,523 B2 | 5/2012 | Tenne et al. |
| 8,187,316 B2 | 5/2012 | Kuppurathanam |
| 8,357,194 B2 | 1/2013 | Majercak |
| 8,372,133 B2 | 2/2013 | Douk et al. |
| 8,394,119 B2 | 3/2013 | Zaver |
| 8,449,600 B2 | 5/2013 | Hartley et al. |
| 8,562,666 B2 | 10/2013 | Bonsignore |
| 8,579,959 B2 | 11/2013 | Ducke |
| 8,597,276 B2 | 12/2013 | Vongphakdy et al. |
| 8,641,748 B2 | 2/2014 | Hebert et al. |
| 8,672,992 B2 | 3/2014 | Orr |
| 8,709,065 B2 | 4/2014 | Chobotov |
| 8,734,501 B2 | 5/2014 | Hartley et al. |
| 8,778,008 B2 | 7/2014 | Amplatz et al. |
| 8,816,247 B1 | 8/2014 | Janardhan et al. |
| 8,864,811 B2 | 10/2014 | Kao |
| 9,078,731 B2 | 7/2015 | Mortarino |
| 9,192,462 B2 | 11/2015 | Vinluan et al. |
| 9,301,864 B2 | 4/2016 | Kao |
| 9,320,590 B2 | 4/2016 | Zaver |
| 9,339,260 B2 | 5/2016 | Eidenschink et al. |
| 9,427,343 B2 | 8/2016 | Bogert |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |

(56) References Cited

U.S. PATENT DOCUMENTS

| | | |
|---|---|---|
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Peterson |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 10,076,428 B2 | 9/2018 | Gorochow |
| 10,206,796 B2 | 2/2019 | Tehrani et al. |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0188344 A1 | 12/2002 | Bolea |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0236406 A1 | 11/2004 | Gregorich |
| 2004/0254637 A1 | 12/2004 | Yang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0148866 A1 | 7/2005 | Gunderson |
| 2005/0228484 A1 | 10/2005 | Stephens et al. |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0064156 A1 | 3/2006 | Thistle |
| 2006/0069424 A1 | 3/2006 | Acosta |
| 2006/0195175 A1 | 8/2006 | Bregulla |
| 2006/0212113 A1 | 9/2006 | Shaolian et al. |
| 2006/0271153 A1 | 11/2006 | Garcia |
| 2006/0287717 A1 | 12/2006 | Rowe |
| 2007/0005127 A1 | 1/2007 | Boekstegers |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0213810 A1 | 9/2007 | Newhauser |
| 2007/0219612 A1 | 9/2007 | Andreas |
| 2007/0219613 A1 | 9/2007 | Kao |
| 2007/0233223 A1 | 10/2007 | Styrc |
| 2007/0233224 A1 | 10/2007 | Leynov |
| 2007/0238979 A1 | 10/2007 | Huynh |
| 2007/0255385 A1 | 11/2007 | Tenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0192588 A1 | 7/2009 | Shin |
| 2009/0198315 A1 | 8/2009 | Boudjemline |
| 2009/0234429 A1 | 9/2009 | Lau |
| 2009/0248133 A1 | 10/2009 | Bloom |
| 2009/0287145 A1 | 11/2009 | Cragg |
| 2009/0297582 A1 | 12/2009 | Meyer et al. |
| 2009/0306761 A1 | 12/2009 | Hebert et al. |
| 2009/0326640 A1 | 12/2009 | Yoshimura |
| 2010/0010619 A1 | 1/2010 | Tischler |
| 2010/0010622 A1 | 1/2010 | Lowe |
| 2010/0069948 A1 | 3/2010 | Veznedaroglu |
| 2010/0161028 A1 | 6/2010 | Chuter |
| 2010/0161036 A1 | 6/2010 | Pintor |
| 2010/0234935 A1 | 9/2010 | Bashiri |
| 2010/0274282 A1 | 10/2010 | Olson |
| 2010/0292777 A1 | 11/2010 | Meyer |
| 2010/0298872 A1 | 11/2010 | Berndt |
| 2010/0324651 A1 | 12/2010 | Holzer |
| 2010/0331972 A1 | 12/2010 | Pintor |
| 2011/0004237 A1 | 1/2011 | Schneider et al. |
| 2011/0184508 A2 | 7/2011 | Burmeister |
| 2011/0264186 A1* | 10/2011 | Berglung ................ A61F 2/86 623/1.11 |
| 2011/0307049 A1 | 12/2011 | Kao |
| 2012/0035714 A1 | 2/2012 | Ducke et al. |
| 2012/0041538 A1 | 2/2012 | White |
| 2012/0065728 A1 | 3/2012 | Gainor et al. |
| 2012/0168022 A1 | 7/2012 | Rasmussen |
| 2012/0191176 A1 | 7/2012 | Nagl |
| 2012/0197377 A1 | 8/2012 | Ditter |
| 2012/0271403 A1 | 10/2012 | Gries |
| 2013/0041454 A1 | 2/2013 | Dobson |
| 2013/0060323 A1 | 3/2013 | McHugo |
| 2013/0123901 A1 | 5/2013 | Connor |
| 2013/0144375 A1 | 6/2013 | Giasolli |
| 2013/0245745 A1 | 9/2013 | Vong et al. |
| 2013/0253572 A1 | 9/2013 | Molaei et al. |
| 2013/0274849 A1 | 10/2013 | Zaver |
| 2013/0345739 A1 | 12/2013 | Brady |
| 2014/0025161 A1 | 1/2014 | Stankus et al. |
| 2014/0200648 A1 | 7/2014 | Newell et al. |
| 2014/0277332 A1 | 9/2014 | Slazas et al. |
| 2014/0277360 A1 | 9/2014 | Gimary et al. |
| 2014/0277376 A1 | 9/2014 | Lorenzo |
| 2014/0277400 A1 | 9/2014 | Wainwright et al. |
| 2014/0336741 A1 | 11/2014 | Connor |
| 2015/0025625 A1* | 1/2015 | Rylski ................ A61F 2/2418 623/2.14 |
| 2015/0045831 A1 | 2/2015 | Allen |
| 2015/0119974 A1 | 4/2015 | Rothstein |
| 2015/0148882 A1 | 5/2015 | Ma et al. |
| 2015/0265400 A1 | 9/2015 | Eidenschink |
| 2015/0320556 A1 | 11/2015 | Levi |
| 2015/0374483 A1 | 12/2015 | Janardham et al. |
| 2016/0030155 A1 | 2/2016 | Cox et al. |
| 2016/0038280 A1 | 2/2016 | Morriss |
| 2016/0058524 A1 | 3/2016 | Tehrani et al. |
| 2016/0235561 A1 | 8/2016 | Wrobel et al. |
| 2017/0007264 A1 | 1/2017 | Cruise et al. |

(56) References Cited

U.S. PATENT DOCUMENTS

| | | |
|---|---|---|
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079813 A1 | 3/2017 | Bar et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0156734 A1 | 6/2017 | Griffin |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0196689 A1 | 7/2017 | Salahieh |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265870 A1 | 9/2017 | Kealey et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281375 A1 | 10/2017 | Longo |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290653 A1* | 10/2017 | Folan .................. A61F 2/04 |
| 2017/0290654 A1 | 10/2017 | Sethna |
| 2017/0290686 A1 | 10/2017 | Sirhan |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0092766 A1 | 4/2018 | Gorochow |
| 2018/0263794 A1 | 9/2018 | Slazas et al. |
| 2018/0333281 A1 | 11/2018 | Tehrani et al. |
| 2019/0015229 A1 | 1/2019 | Fukutaki |
| 2019/0021888 A1 | 1/2019 | Tehrani |
| 2019/0053899 A1 | 2/2019 | Levi |
| 2019/0224008 A1 | 7/2019 | Bressloff |

FOREIGN PATENT DOCUMENTS

| | | |
|---|---|---|
| EP | 3 311 782 A1 | 4/2018 |
| JP | 2013-541358 A1 | 11/2013 |
| WO | 01/35864 A1 | 5/2001 |

OTHER PUBLICATIONS

Notification of Reasons for Refusal issued in corresponding Japanese Patent Application No. 2020-024204 dated Feb. 2, 2021 (only English translation submitted).

* cited by examiner

1000 providing a braid having a proximal end, a distal end, and a lumen formed therebetween by one or more braided wires
1010 positioning a first expansion ring with the proximal end, the first expansion ring configured to be self-expanding and apply an outward radial force to the proximal end of the braid
1020 positioning a second expansion ring at a distal end of the braid, the second expansion ring configured to be self-expanding and apply an outward radial force to the distal end of the braid
1030 engaging at least one of the first and second expansion rings to a delivery wire
1040 delivering the braid to an aneurysm by distally advancing the delivery wire
1050

Fig. 10

BRAIDED STENT SYSTEM WITH ONE OR MORE EXPANSION RINGS

FIELD

The present disclosure relates generally to treatment of certain defects in a vasculature of a patient and more particularly, to self-expanding braided stents to a treatment site in a vasculature of a patient.

BACKGROUND

Stents are understood as tubular reinforcements that can be inserted into a blood vessel to provide an open path within the blood vessel. Stents have been widely used in intravascular angioplasty treatment of occluded cardiac arteries, wherein the stent may be inserted after an angioplasty procedure to prevent restenosis of the artery. Stents are often deployed by use of delivery devices which cause the stent to open with the objective of reinforcing the artery wall and provide a clear through-path in the artery thereby preventing restenosis.

However, the weakness and non-linear nature of the neurovasculature limits the applicability of such stents in procedures, for example, in repairing neurovascular defects. Furthermore, known delivery methods are less useful in vasoocclusive surgery, particularly when tiny vessels, such as those found in the brain, are to be treated.

In addition, single wire braided stents have some key advantages such as lower crimp profiles and require lower forces to track the devices during delivery in the vasculature. These stents are manufactured by braiding a wire in a pattern (e.g., cylindrical) and are typically manufactured of a self-expanding material, such as Nitinol. A significant drawback of these devices is that they have very low radial expansion forces resulting in stent migration and difficulty in accurately placing the device.

Accordingly, a need exists for a stent that can be used with delivery techniques in vasoocclusive treatment of neurovascular defects that provides selective, accurate reinforcement in the vicinity of the neurovascular defect. A need also exists for a stent that reduces trauma or risk of rupture to the blood vessel.

It is with respect to these and other considerations that the various embodiments described below are presented.

SUMMARY

In some aspects, the present disclosure relates to a braided stent system that can include a braid with a proximal end, a distal end, and a lumen formed therebetween. The braid can be formed from one or more wires woven to comprise interstices. A first expansion ring can be connected to the proximal end of the braid. A second expansion ring can be connected to the distal end of the braid. Each expansion ring can include a frame that imparts an outwardly expanding radial force to the braid. The frame can include a plurality of elongate members interconnected by one or more intersections.

In some aspects, the proximal end and the distal end each comprise looped ends formed from the one or more wires.

In some aspects, the elongate members of each of the first or second expansion rings are interwoven into and out of adjacent looped ends of the braid.

In some aspects, intersections of each of the first or second expansion rings are interwoven sequentially whereby each intersection is connected or in communication with a respective looped end of the braid.

In some aspects, intersections of each of the first or second expansion rings are interwoven sequentially whereby each intersection is wrapped around or hooked with a respective looped end of the braid.

In some aspects, the elongate members of each of the first or second expansion rings are interwoven sequentially to adjacent looped ends of the braid in the form of a zig-zag shaped assembly.

In some aspects, the elongate members of each of the first or second expansion rings are interwoven sequentially to adjacent looped ends of the braid in the form of a zig-zag shaped assembly.

In some aspects, the first expansion ring includes one or more radiopaque bands connected with one or more corresponding elongate members proximal of the proximal end of the braid.

In some aspects, the first expansion ring includes one or more radiopaque bands connected with one or more corresponding elongate members adjacent a respective intersection connected with a respective looped end and proximal of the proximal end.

In some aspects, the second expansion ring includes one or more radiopaque bands connected with one or more corresponding elongate members distal of the distal end of the braid.

In some aspects, the second expansion ring also includes one or more radiopaque bands connected with one or more corresponding elongate members adjacent a respective intersection connected with a respective looped end and distal of the distal end.

In some aspects, at least one of the first and second expansion ring also includes one or more radiopaque bands connected with one or more corresponding elongate members and corresponding looped end of the braid.

In some aspects, each elongate member is connected to the corresponding looped end of the braid by wrapping or encircling the respective radiopaque band thereabout.

In some aspects, each elongate member is oriented parallel to a respective portion of the wire of the corresponding looped end connected to the radiopaque band.

In some aspects, at least one of the first or second expansion rings comprises a clip that is mechanically connected to one or more of the looped ends.

In some aspects, one end point of the first or second expansion ring is provided per looped end of the respective proximal or distal end.

In some aspects, each expansion ring is self-expanding.

In some aspects, the frame of each expansion ring formed by the elongate members and intersections comprise one of a zig-zag shape, a "V" shape, a "U" shape, a "W" shape, or a double "U" shape.

In some aspects, a method of using a braid is disclosed. The method includes providing a braid having a proximal end, a distal end, and a lumen formed therebetween by one or more braided wires; positioning a first expansion ring with the proximal end, the first expansion ring configured to be self-expanding and apply an outward radial force to the proximal end of the braid; positioning a second expansion ring at a distal end of the braid, the second expansion ring configured to be self-expanding and apply an outward radial force to the distal end of the braid; engaging at least one of the first and second expansion rings to a delivery wire; and delivering the braid to an aneurysm by distally advancing the delivery wire.

In some aspects, the step of positioning the first expansion ring at the proximal end of the braid includes sequentially translating one or more elongate members of the first expansion ring into and out of adjacent looped ends of the proximal end of the braid.

In some aspects, the step of positioning the second expansion ring at the distal end of the braid includes sequentially translating one or more elongate members of the second expansion ring into and out of adjacent looped ends of the distal end of the braid.

In some aspects, the step of positioning the first expansion ring at the proximal end of the braid includes positioning one or more intersections of the first expansion ring until each intersection is connected or in communication with a respective looped end of the proximal end of the braid.

In some aspects, the method also includes wrapping around or hooking each intersection with a respective looped end of the braid.

In some aspects, the step of positioning the second expansion ring at the distal end of the braid includes positioning one or more intersections of the second expansion ring until each intersection is connected or in communication with a respective looped end of the distal end of the braid.

In some aspects, the method also includes wrapping around or hooking each intersection with a respective looped end of the braid.

In some aspects, the method also includes connecting one or more radiopaque bands with one or more corresponding elongate members proximal of the proximal end of the braid.

In some aspects, the method also includes connecting one or more radiopaque bands with one or more corresponding elongate members adjacent a respective intersection of the first expansion ring connected with a respective looped end of the braid and proximal of the proximal end.

In some aspects, the method also includes connecting one or more radiopaque bands with one or more corresponding elongate members adjacent a respective intersection of the first expansion ring connected with a respective looped end of the braid and proximal of the proximal end.

In some aspects, the method also includes wherein at least one of the first and second expansion ring also includes one or more radiopaque bands connected with one or more corresponding elongate members and corresponding looped end of the braid.

In some aspects, the method also includes connecting each elongate member to a corresponding looped end of the braid by wrapping or encircling the respective radiopaque band thereabout.

In some aspects, the method also includes orienting parallel an elongate member to a respective wire of the braid extending from a corresponding looped end and connected to the radiopaque band.

In some aspects, the method also includes connecting one or more of the looped ends or wire of the braid to a void of the clip of the first or second expansion rings.

In some aspects, the method also includes forming the frame of each expansion ring by the elongate members and intersections into one of a zig-zag shape, a "V" shape, a "U" shape, a "W" shape, or a double "U" shape.

In some aspects, the braid is a mesh flow diverter.

In some aspects, the method also includes increasing a radial expansion force of the braid by attaching the first expansion ring at the proximal end and attaching the second expansion ring at the distal end.

BRIEF DESCRIPTION OF THE DRAWINGS

Reference will now be made to the accompanying drawings, which are not necessarily drawn to scale.

FIG. 10 shows a flow diagram depicting an example method of this disclosure.

DETAILED DESCRIPTION

Figure 1:
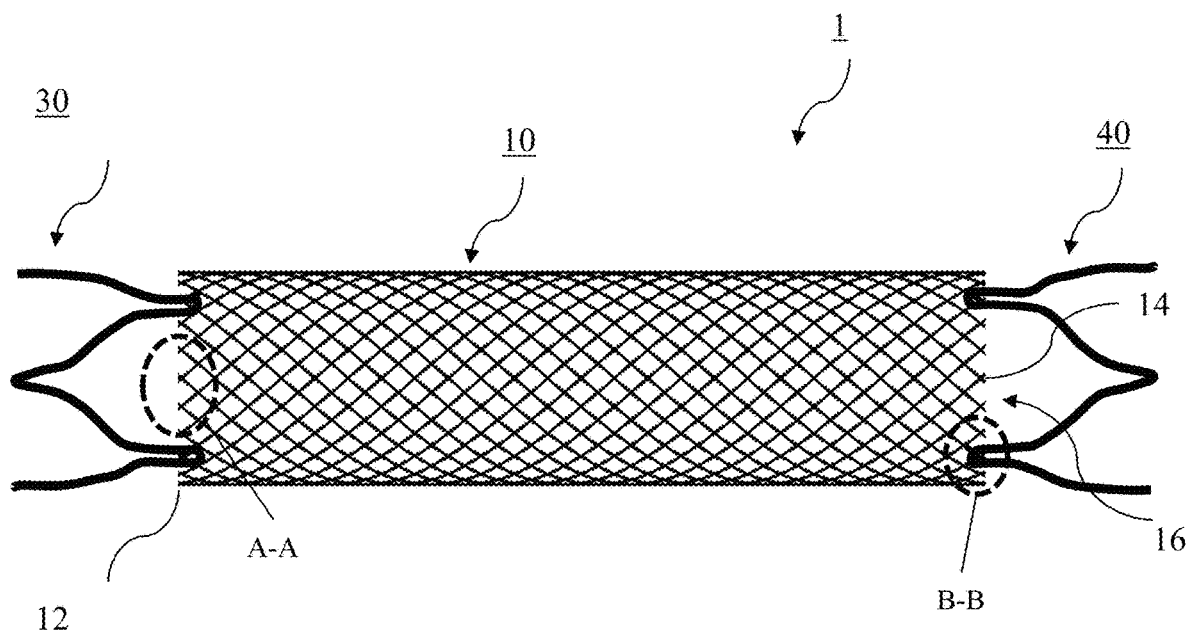
FIG. 1 depicts a side plan view of exemplary self-expanding braid assembled with example expansion rings at respective proximal and distal ends of the example braid.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

Braids may be formed from a plurality of elongate members (e.g. metal wires, polymeric fibers, or strands of material) and these members can be very useful in treatment of neurovascular defects. However, when such braided members are intended to be self-expanding in a lumen of a stent body, known manners of activation of the initially expanding end struggle to adequately, reliably, and fully open so that the initially expanding end can be used as an anchor point. Moreover, braids have been known to exhibit high internal friction that resists the inherent radial expansion force of the self-expanding braid when being deployed to an opened state. More specifically, the relatively high internal friction can render it difficult to open the initially expanding end of the stent which results in deficiencies in anchoring and deployment. This is particularly true for braids delivered to the desired vessel location through use of a delivery sheath, microcatheter, or the like, since in a closed state (e.g.

compressed or crimped) the stent body typically exhibits friction between the braided members and the delivery sheath or microcatheter.

In practice, braids can be delivered to a particular vessel by advancing a blunt surface against a proximal end of the braid causing the braid to axially compress and expand radially. This expansion within the delivery sheath or microcatheter can result in an increased normal force being applied to the inner surface of the delivery sheath, microcatheter, or the like thereby also increasing friction caused by the braid.

Known solutions to these issues have depended on factors such as material, size, cell design, internal friction, and extra manipulation by the end-user to reliably, quickly and adequately open the braids. In turn, success of the braid relied heavily on end-user accuracy in delivery which unnecessarily increases risk of injury to the patient.

Moreover, such braided, self-expanding stents can be difficult to recapture after being delivered and/or deployed. It is to be understood that a "self-expanding" stent is a stent wherein the particular stent fully deploys upon emerging through a delivery device such as a sheath, microcatheter, or the like. In this respect, when a self-expanding stent body emerges, unrestrained outside of the respective delivery device, the self-expanding braid should expand and be deployed in the vasculature. However, due to the referenced radial forces and friction, stent deployment and recapture following deployment is difficult. The present inventors have devised delivery systems that overcome these problems, see at least U.S. patent application Ser. No. 15/281, 974, published, as U.S. Patent Publication No. 2018/ 0092766 A1 and issued as U.S. Pat. No. 10,292,851 B2, incorporated herein by reference.

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

Turning to FIG. 1, the herein disclosed expansion ring 30, 40 is depicted in a side plan view with example braid 10. The depicted system 1 resolves these and other issues by providing a secure, mechanical attachment between ring 30, 40 and the corresponding, braid 10 that increases an outwardly extending radial expansion force of a proximal 12 and distal 14 end and/or a lumen 16 defined therebetween. Each ring 30, 40 includes a frame with a plurality of interconnected elongate members 38 that collectively cause the ring to connect itself with the respective proximal 12 or distal 14 end of braid 10. Upon interconnection of elongate members 38 of the frame with the proximal 12 or distal 14 end of braid 10, the ring 30, 40 is capable of imparting an outwardly expanding radial force to the braid 10. In some aspects, as shown more particularly in FIG. 3, the respective end of each ring 40 is connected by mechanically securing a clip 35 of each ring 40 to be interlaced and/or interwoven with looped ends 18 of braid 10. In some embodiments, elongate members 36, 38 of each of the first or second expansion rings 30, 40 are interwoven into and out of adjacent looped ends 18 of the braid 10. Assembling one or more rings 30, 40 with braid 10 results in relatively easy delivery without the need for accurate positioning of ring 30, 40 with braid 10.

Figure 2:
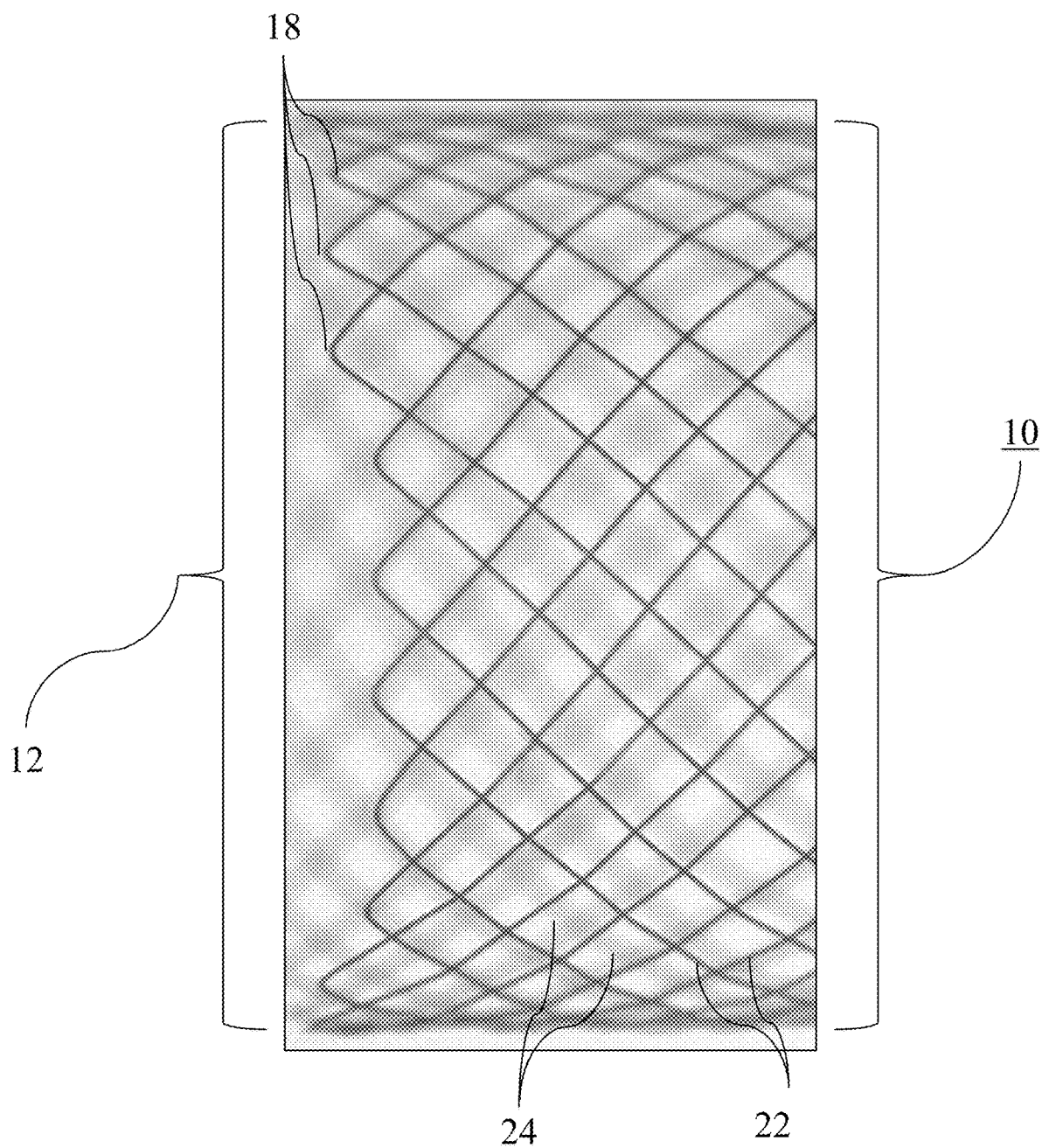
FIG. 2 is a close-up view of plane A-A of FIG. 1 depicting an exemplary proximal end of the braid with corresponding looped ends.

FIG. 2 depicts a close-up view of plane A-A of FIG. 1 depicting an exemplary proximal end 12 of braid 10 with corresponding looped ends 18. It can also be seen that wire or wires 22 are braided to form the atraumatic, looped ends 18. It is understood that the distal end 14 can also have the same or similar looped ends 18.

Figure 3:
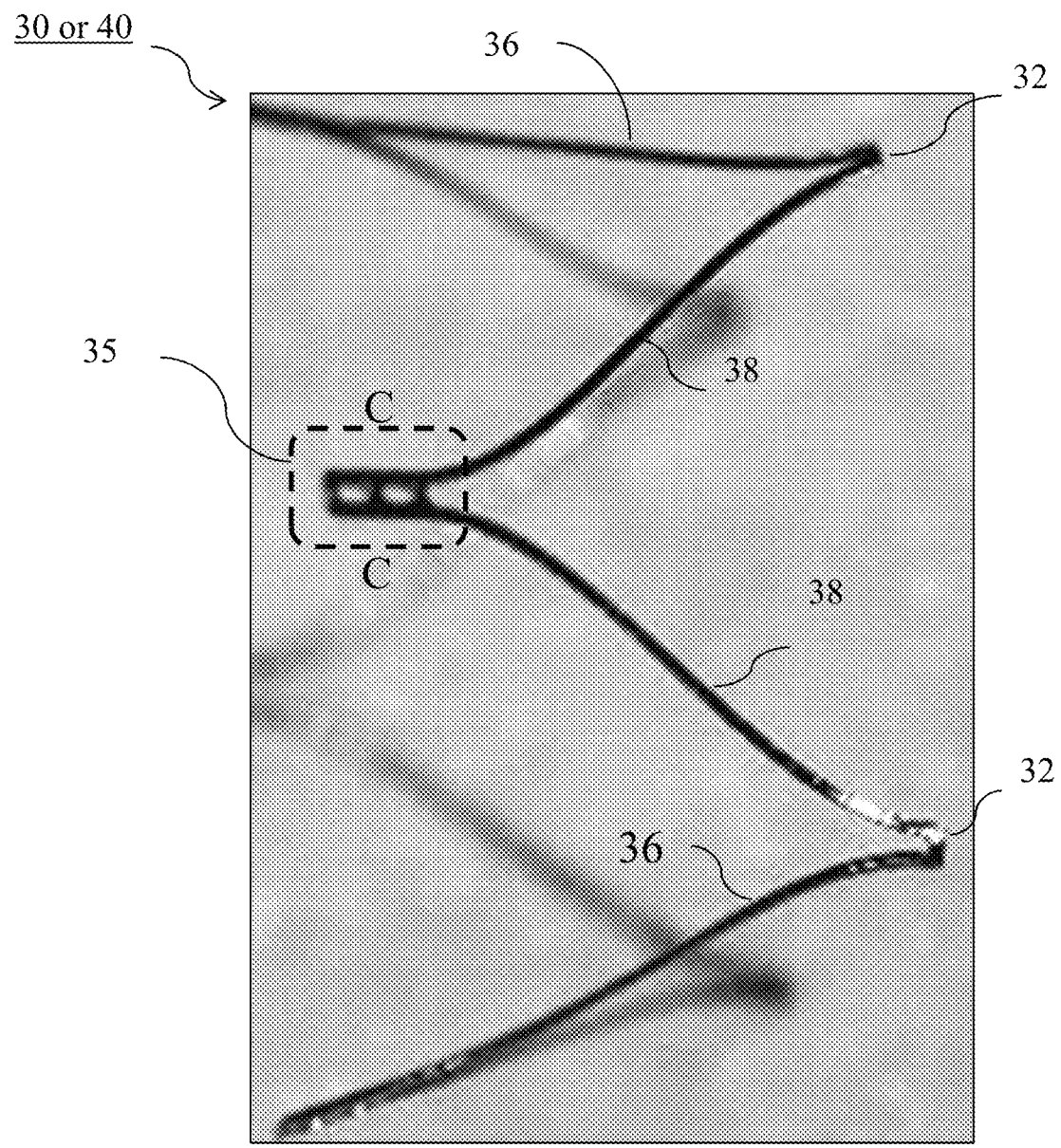
FIG. 3 is a perspective of an exemplary expansion ring prior to being assembled with a braid of this disclosure.

Turning to FIG. 3, a perspective view of exemplary ring 30, 40 is shown with a plurality of interconnected elongate members 36, 38. While each frame of ring 30, 40 that is formed by interconnected elongate members 36, 38 may be V-shaped as in FIG. 3, it is understood that the frame of ring 30, 40 can also be arranged in other bowed orientations. In this regard, members 36, 38 may include a curved or arched portion that bows with a predetermined resistance to compression. Each frame of rings 30, 40, including respective members 36, 38, may have the same or a different resistance so that ring 30, 40 can be individualized for the specific vasculature implementation.

In a compressed, unexpanded state inside microcatheter 10, each 30, 40 is operable to assemble with looped ends 18 of braid 10 while also providing outward expanding radial forces to counter the inwardly applied compression in the compressed state. Members 36, 38 and its constituent features, including intersection 32 and/or any preformed shape such as the bowed V-shape of FIG. 3, may be formed of a superelastic material, such as a nickel-titanium alloy or Nitinol, or may be formed of a non-superelastic material, such as spring steel or MP35N, an alloy of 35% nickel, 35% cobalt, 20% chromium, and 10% molybdenum, by weight. Members 36, 38 may also be formed from a shape memory material having a shape memory position in the opened state.

Figure 4:
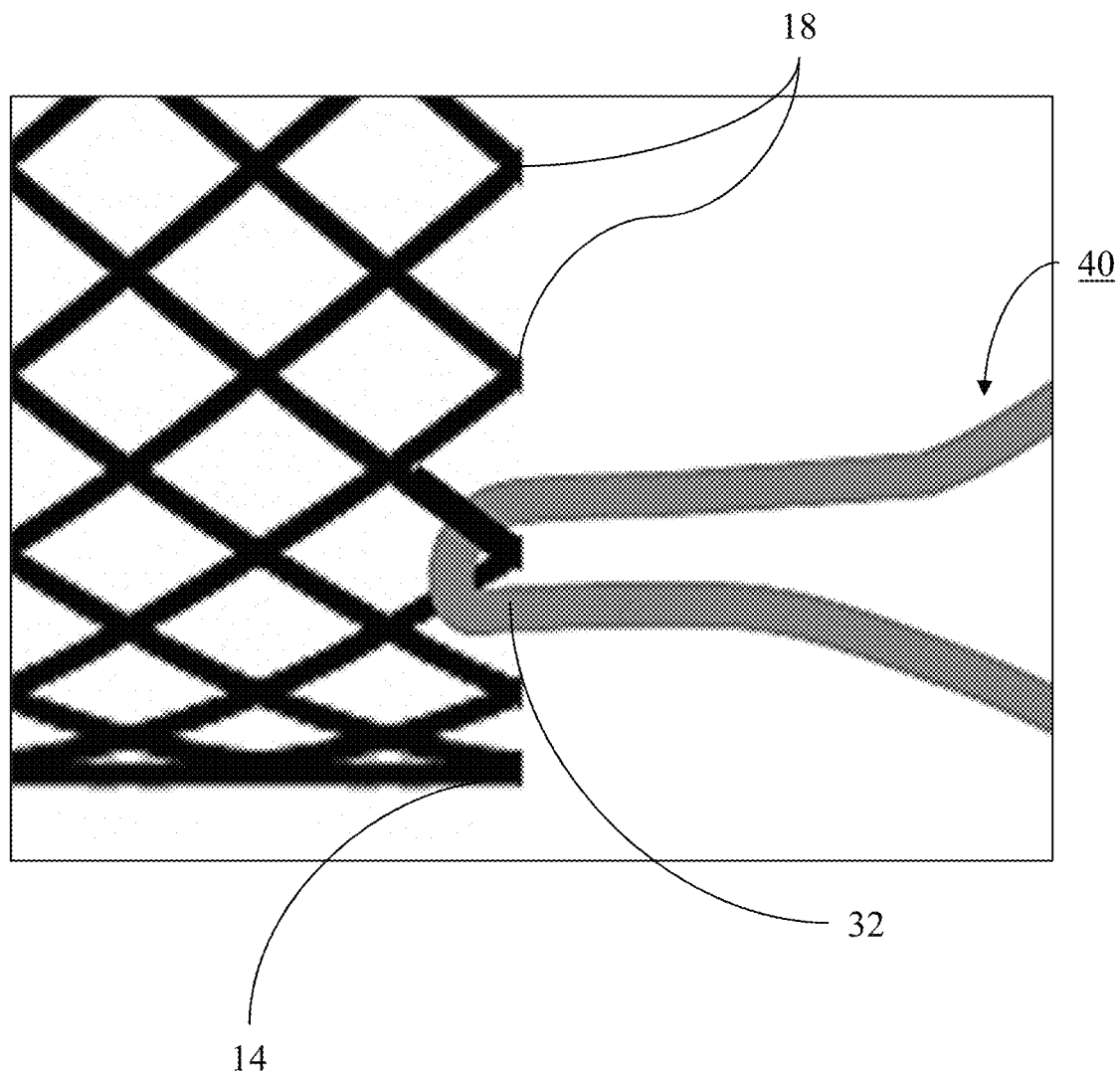
FIG. 4 is a close-up view of plane B-B of FIG. 1 showing certain features of one of the depicted expansion rings weaved through interstices of an example braid.
Figure 6:
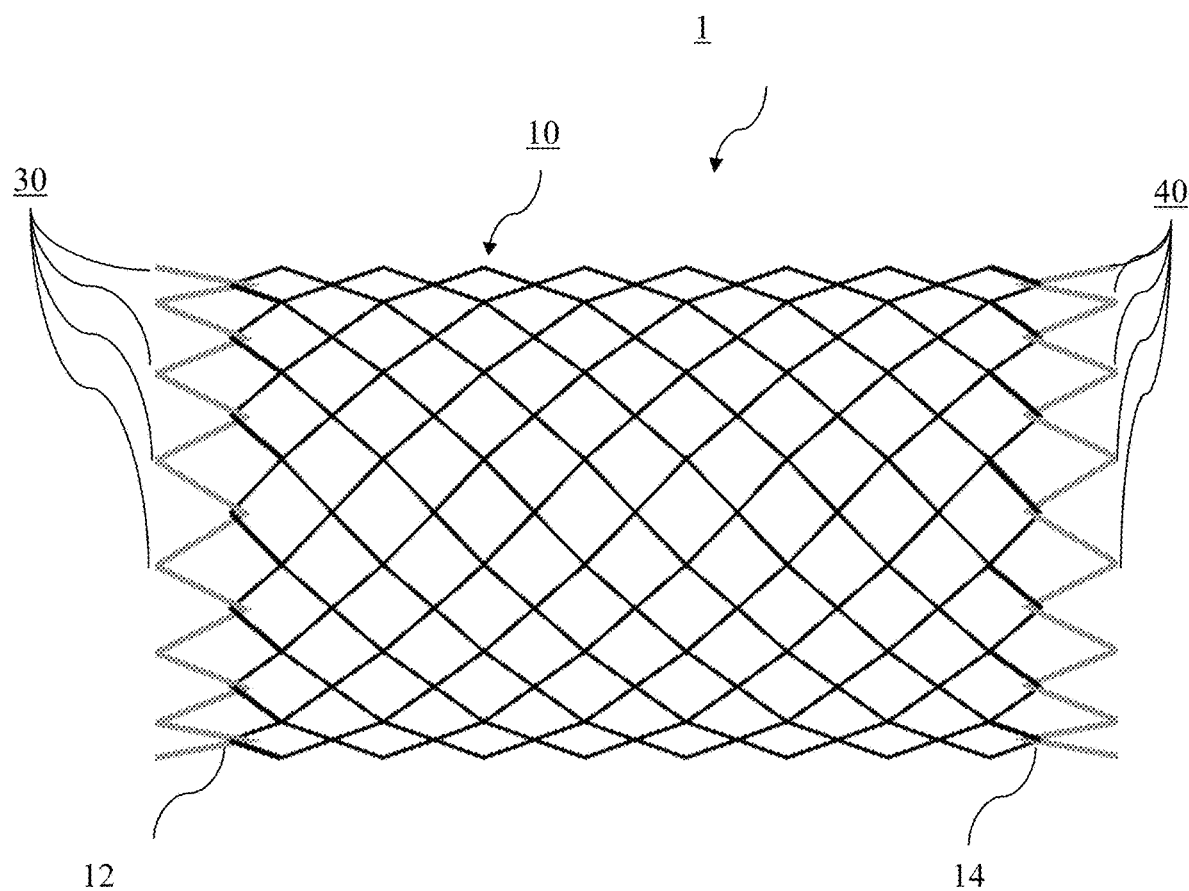
FIG. 6 depicts a side plan view of exemplary expansion rings when assembled at proximal and distal ends of an example braid.

FIG. 4 depicts a close-up view of plane B-B of FIG. 1 depicting an intersection 32 of ring 40 interlaced with a looped end 18 of distal end 14 of braid 10. More specifically, members 38, 36 can be seen being joined together at intersection 32. Ring 40, including members 36, 38 and corresponding intersection 32, can be woven with end 18 in a variety of ways. For example, member 38 can be interwoven into and out of adjacent looped ends 18 of the braid 10, including sequentially through consecutive looped ends 18, as shown in FIG. 6. In this respect, intersection 32 can be in a zig-zag shape and/or wrapped around or hooked with a respective looped end 18 of the braid 10. While ring 30 is not depicted in FIG. 4 with its intersection 32 connected to a corresponding looped end of proximal end 12, it is contemplated that ring 30 would similarly connect with end 12 as shown in FIG. 4.

Figure 5:
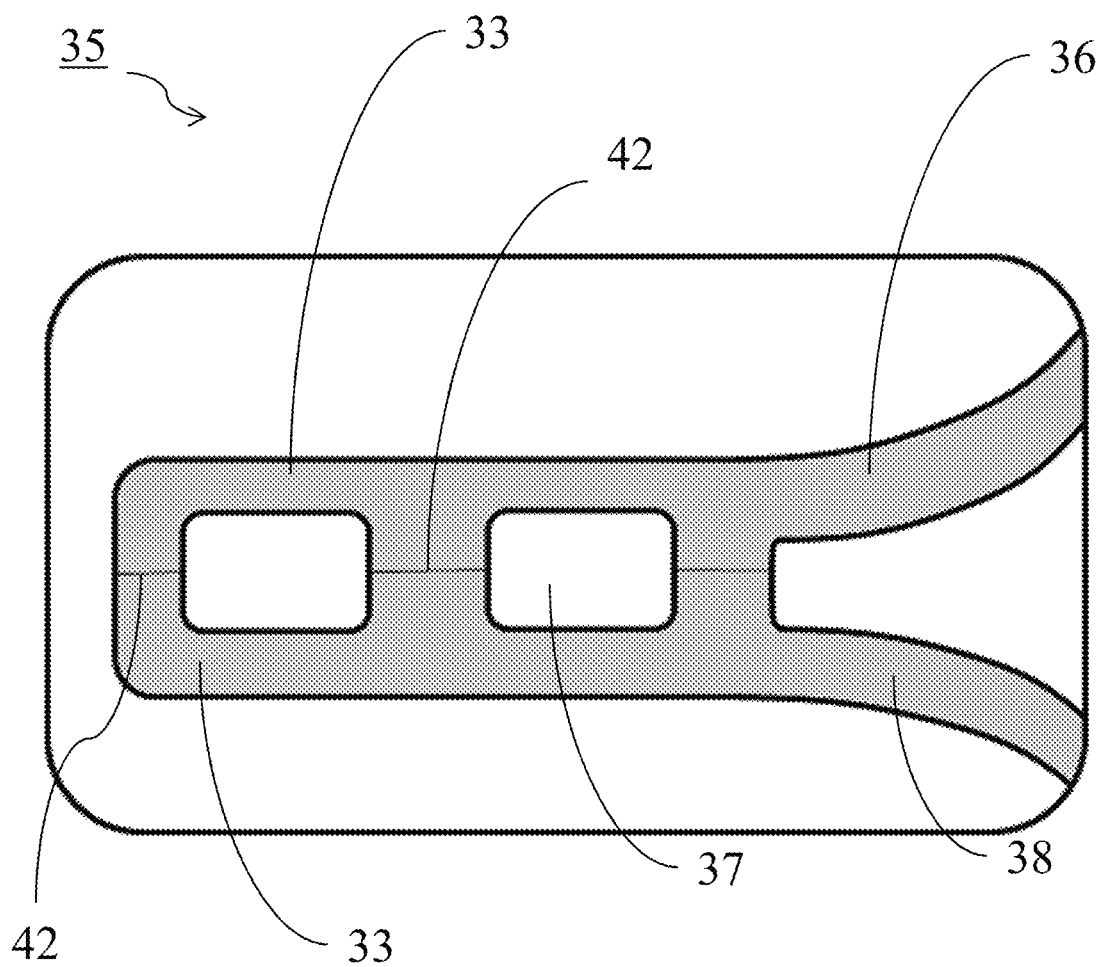
FIG. 5 is a close-up view of plane C-C of FIG. 3 showing an example clip of an example expansion ring of this disclosure.

FIG. 5 is a close-up view of an example clip 35 of a ring 30, 40. The frame of ring 30, 40 may include members 38, 36 joined together, as shown, at first intersection 32, whereby intersection 32 can be said clip 35. While members 38, 36 are seen integrally formed with each other in FIG. 5, rings 30, 40 are not so limited and members 38, 36 may be removably attached to each other or otherwise connected. Members 38, 36 may also be adhered to each other, crimped, or welded to form connections 42. Additionally, if one or more fasteners are used in a particular implementation with connections 42, they can be removably connected or welded, soldered, and/or crimped. Fasteners and/or members 38, 36 can be formed of a radiopaque metal, such as platinum or tantalum, or may be formed of a non-radiopaque material, such as stainless steel.

By adding clip 35 to the intersection of members 38, 36, each ring 30, 40 can be interlaced with looped ends 18 without a permanent or rigid attachment thereto (e.g., welding, soldering or a chemical adhesive). Intersection 32, including clip 35, may also include a rotatable and/or twistable hinge-type coupling so that each ring 30, 40 is capable of flexing a predetermined amount when braid 10 and ring 30, 40 is in use. One or more elongate members 33 may extend from intersection 32, including from members 38, 36, and terminate at connection 42 opposite intersection 32. Elongate members 33 are shown substantially aligned and offset from each other while being joined at one or more connections 42 to form one or more corresponding voids 37 therebetween through which wires 22 can pass.

In some aspects, elongate members 33 can be passed through and/or interlaced with wire 22 and corresponding looped end 18 and then joined at the one or more respective connections 42. In those embodiments where more than one void 37 is provided, one or more multiple looped ends 18 or passes by wire 22 may be arranged in or in connection with voids 37 so that clip 35 may be mechanically attached to proximal end 12 or distal end 14, respectively. The one or more connections 42 between elongate members 33 may be formed from a weld, crimp, band, clamp, or adhesive.

FIG. 6 depicts a side plan view of rings 30, 40 being selectively positioned at ends 12, 14. In the zig-zag configuration of this embodiment, it is understood that the rings 30, 40 can be interwoven or otherwise interconnected so that respective intersections 32 of each ring 30, 40 are in communication with looped ends 18 of braid 10. In certain embodiments, for every looped end 18 a corresponding intersection 32 can be provided by either of rings 30, 40. It is to be understood that the embodiment of FIG. 6 is not intended to be limiting and any number of rings 30,40 and/or interlaced with looped ends 18. For example, intersections 32, including its elongate members 36, 38, can be pulled or translated or otherwise advanced with respect to looped ends 18 of braid 10 so as to be interwoven sequentially to adjacent looped ends 18 of the braid 10 in the form of a zig-zag shaped assembly.

Figure 7:
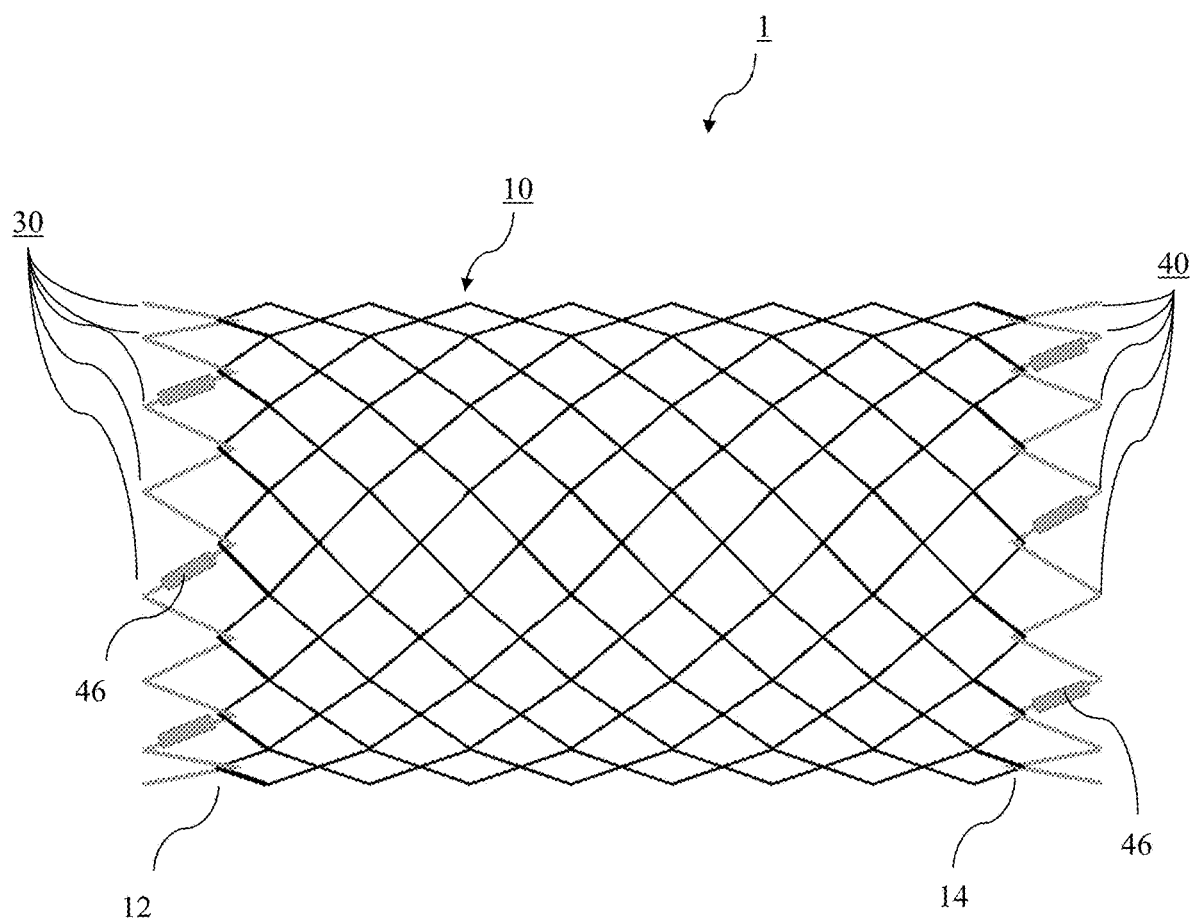
FIG. 7 depicts a side plan view of exemplary expansion rings when assembled at proximal and distal ends of an example braid.

FIG. 7 depicts an aspect of a braid 10 of this disclosure with rings, 30, 40 having radiopaque bands 46. In particular, one or more radiopaque bands 46 can be connected with one or more corresponding elongate members 38 of rings 30, 40. In some aspects, band 46 can be positioned around or otherwise circumferentially around elongate member 38 or member 36 (e.g., axially aligned on the outer surface of a respective member). In some embodiments, the band 46 can be in contact with braid 10 at looped end 18 or can be just distal or proximal thereof.

Figure 8:
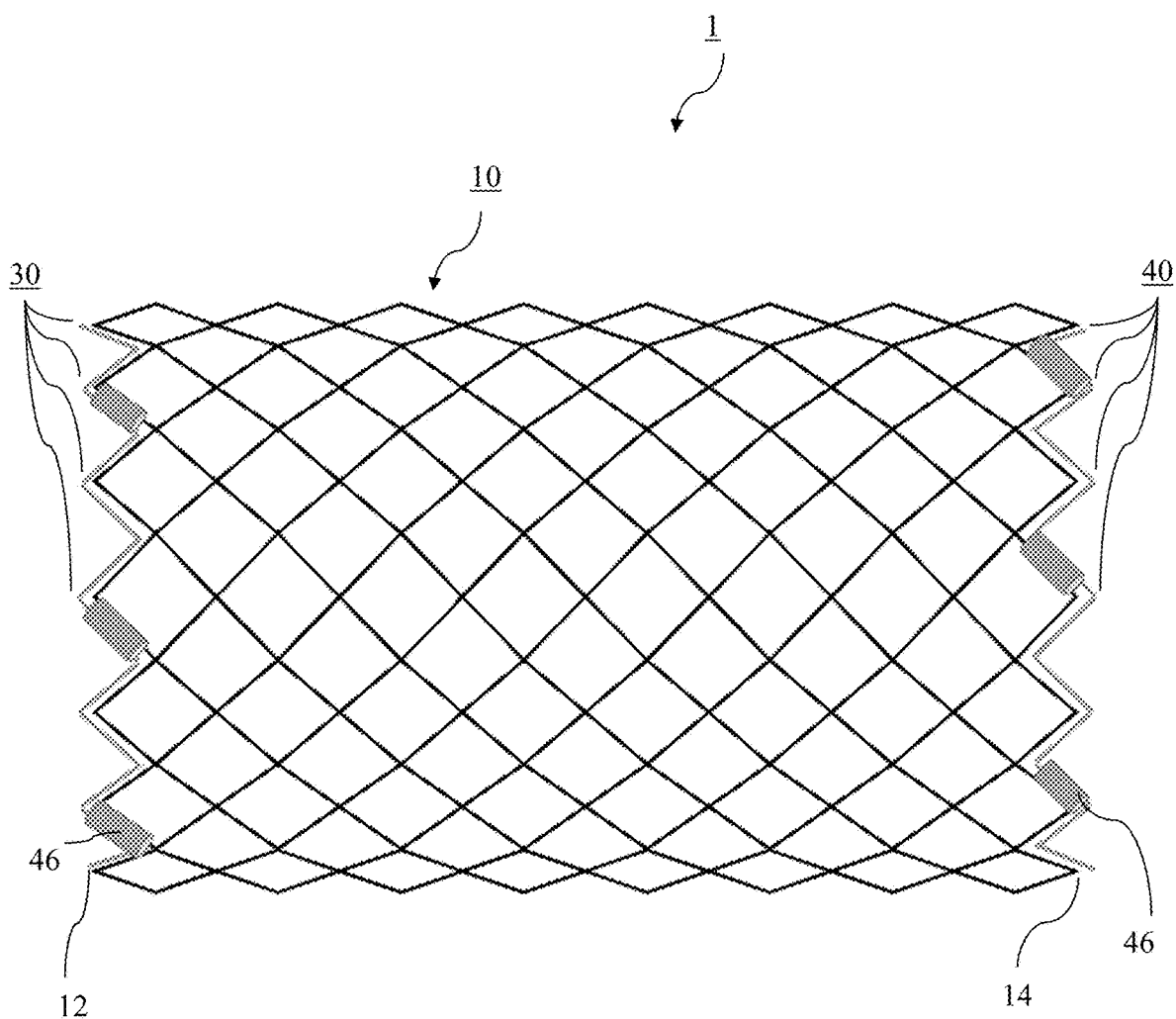
FIG. 8 depicts a side plan view of exemplary expansion rings when assembled at proximal and distal ends of an example braid.

FIG. 8 depicts an aspect of a braid 10 similar the example of FIG. 7. However, in the example depicted in FIG. 8, bands 46 can be axially aligned with both member 38 or 36 and wire 22 just proximal or distal of respective looped end 18 so that the "zig-zag" shape is aligned with corresponding shape of wire 22 of the proximal 12 or distal 14 end. In certain examples, one or more bands 46 can be wrapped around both the respeFctive wire 22 and elongate member 36 or 38 whereby each of wire and member 36 or 38 are therefore also axially aligned and possibly also in contact.

Figure 9:
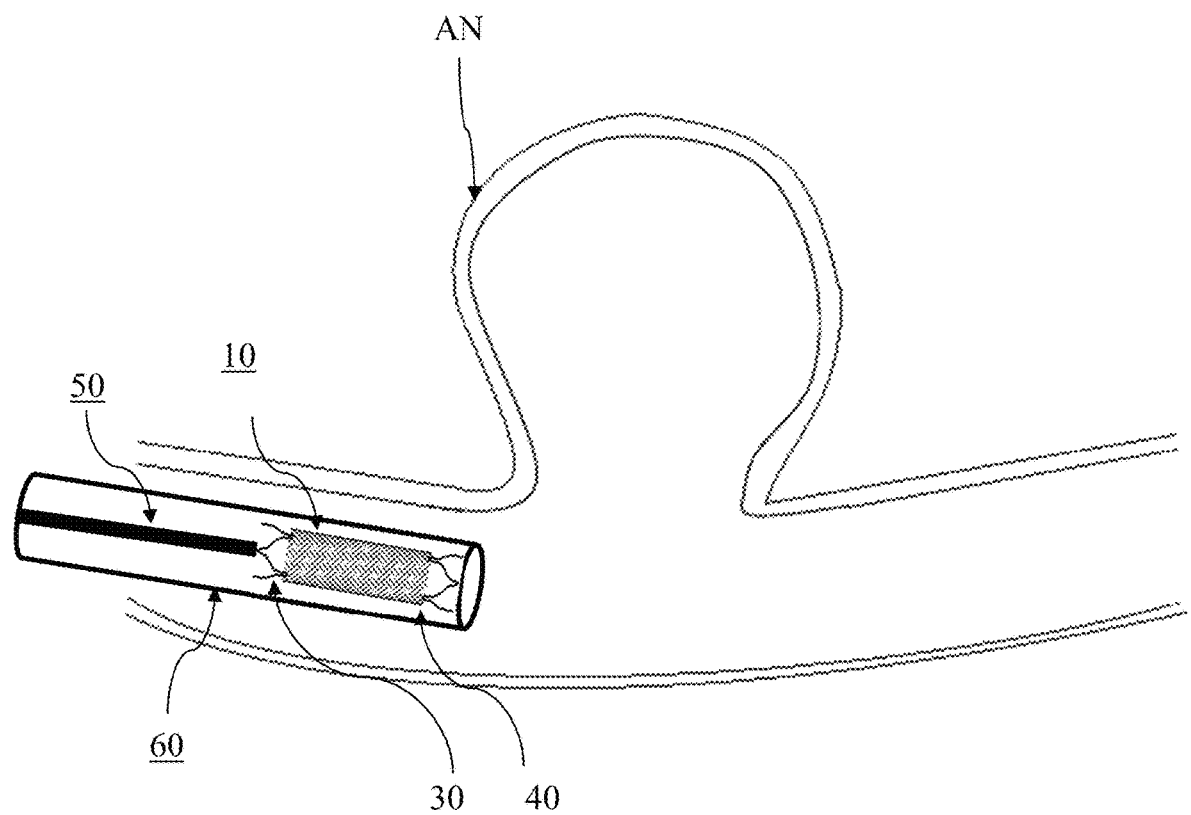
FIG. 9 depicts an example endovascular medical system for use in treating an aneurysm with an example braid.

FIG. 9 depicts an example endovascular medical system for use in treating an aneurysm AN with the herein disclosed example braid 10. During use, a physician or interventionalist endovascularly introduces a guidewire 50 through the vasculature, typically in an artery located in the groin or by direct access through the carotid artery. The guidewire 50 is advanced through the vasculature to the aneurysm. Once the guidewire 50 is properly positioned, a microcatheter 60 tracks distally over the guidewire passing through a lumen defined axially through the microcatheter 60. Once properly positioned (e.g., adjacent or otherwise near the neck of the aneurysm AN, the braid 10 and corresponding expansion rings 30, 40 can be distally advanced towards the aneurysm AN for treatment.

FIG. 10 shows an example method 1000 for using a braid. The method can include step 1010 providing a braid having a proximal end, a distal end, and a lumen formed therebetween by one or more braided wires. Step 1020 can include positioning a first expansion ring with the proximal end, the first expansion ring configured to be self-expanding and apply an outward radial force to the proximal end of the braid. Step 1030 can include positioning a second expansion ring at a distal end of the braid, the second expansion ring configured to be self-expanding and apply an outward radial force to the distal end of the braid. Step 1040 can include engaging at least one of the first and second expansion rings to a delivery wire. Step 1050 can include delivering the braid to an aneurysm by distally advancing the delivery wire.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The descriptions contained herein are examples illustrating the solution and are not intended to limit the scope. As described herein, the solution contemplates many variations and modifications of a system, device, and/or method that can be used to analyze one or more clots and individualize treatment based on the analysis. Variations can include but are not limited to alternative geometries of elements and components described herein, utilizing any of numerous materials for each component or element (e.g. radiopaque materials, memory shape metals, etc.), utilizing additional components, utilizing additional components to perform functions described herein, or utilizing additional components to perform functions not described herein, for example. These modifications would be apparent to those having ordinary skill in the art to which this invention relates and are intended to be within the scope of the claims which follow.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. An endovascular system comprising a self-expanding braid for treating an aneurysm, the system comprising:
   a braid comprising a proximal end, a distal end, and a lumen formed therebetween, the braid formed from one or more wires woven to comprise interstices, the proximal end and the distal end each comprise looped ends formed from the one or more wires;
   a first expansion ring connected to the proximal end of the braid;
   a second expansion ring connected to the distal end of the braid;
   wherein, each expansion ring comprises a frame that imparts an outwardly expanding radial force to the braid, the frame comprising a plurality of elongate members interconnected by one or more intersections, the elongate members of the first or second expansion rings being interwoven into and out of adjacent looped ends of the braid with a remainder of the respective first and second expansion ring disposed external to the braid;
   wherein there is one end point of the first or second expansion ring per looped end of the respective proximal or distal end.

2. An endovascular system comprising a self-expanding braid for treating an aneurysm, the system comprising:
   a braid comprising a proximal end, a distal end, and a lumen formed therebetween, the braid formed from one or more wires woven to comprise interstices, the proximal end and the distal end each comprise looped ends formed from the one or more wires;
   a first expansion ring connected to the proximal end of the braid;
   a second expansion ring connected to the distal end of the braid;
   wherein, each expansion ring comprises a frame that imparts an outwardly expanding radial force to the braid, the frame comprising a plurality of elongate members interconnected by one or more intersections, the elongate members of the first or second expansion rings being interwoven into and out of adjacent looped ends of the braid with a remainder of the respective first and second expansion ring disposed external to the braid,
   wherein intersections of each of the first or second expansion rings are interwoven sequentially whereby each intersection is connected or in communication with a respective looped end of the braid.

3. An endovascular system comprising a self-expanding braid for treating an aneurysm, the system comprising:
   a braid comprising a proximal end, a distal end, and a lumen formed therebetween, the braid formed from one or more wires woven to comprise interstices, the proximal end and the distal end each comprise looped ends formed from the one or more wires;
   a first expansion ring connected to the proximal end of the braid;
   a second expansion ring connected to the distal end of the braid;
   wherein, each expansion ring comprises a frame that imparts an outwardly expanding radial force to the braid, the frame comprising a plurality of elongate members interconnected by one or more intersections, the elongate members of the first or second expansion rings being interwoven into and out of adjacent looped ends of the braid with a remainder of the respective first and second expansion ring disposed external to the braid,
   wherein intersections of each of the first or second expansion rings are interwoven sequentially whereby each intersection is wrapped around or hooked with a respective looped end of the braid.

4. The system of claim 1, wherein the first expansion ring or second expansion ring further comprises:
   one or more radiopaque bands connected with one or more corresponding elongate members proximal of the proximal end or distal of the distal end of the braid.

5. The system of claim 1, wherein the first expansion ring or the second expansion ring further comprises:
   one or more radiopaque bands connected with one or more corresponding elongate members adjacent a respective intersection connected with a respective looped end and proximal of the proximal end or distal of the distal end.

6. The system of claim 1, wherein at least one of the first and second expansion ring further comprises:
   one or more radiopaque bands connected with one or more corresponding elongate members and corresponding looped end of the braid.

7. The system of claim 1, wherein at least one of the first or second expansion rings comprises a clip that is mechanically connected to one or more of the looped ends.

* * * * *